United States Patent
Adams (10) Patent No.: US 10,732,135 B2
(45) Date of Patent: Aug. 4, 2020

(54) SYSTEM AND METHOD FOR DETERMINING ONE OR MORE FLUID CONCENTRATIONS IN A FLUID STREAM

(71) Applicant: Multicore Technologies, LLC, Orlando, FL (US)

(72) Inventor: Christian Adams, Yalaha, FL (US)

(73) Assignee: Multicore Technologies, LLC, Orlando, FL (US)

( * ) Notice: Subject to any disclaimer, the term of this patent is extended or adjusted under 35 U.S.C. 154(b) by 131 days.

(21) Appl. No.: 15/736,160

(22) PCT Filed: Jun. 16, 2016

(86) PCT No.: PCT/US2016/037848
§ 371 (c)(1),
(2) Date: Dec. 13, 2017

(87) PCT Pub. No.: WO2016/205495
PCT Pub. Date: Dec. 22, 2016

(65) Prior Publication Data
US 2018/0188196 A1 Jul. 5, 2018

Related U.S. Application Data

(60) Provisional application No. 62/180,099, filed on Jun. 16, 2015.

(51) Int. Cl.
*G01N 15/00* (2006.01)
*G01N 25/22* (2006.01)
(Continued)

(52) U.S. Cl.
CPC ............ *G01N 25/22* (2013.01); *G01K 11/32* (2013.01); *G01N 25/28* (2013.01); *G01N 27/16* (2013.01);
(Continued)

(58) Field of Classification Search
CPC .............. G01N 1/2247; G01N 15/06; G01N 2021/1704; G01N 2021/8578;
(Continued)

(56) References Cited

U.S. PATENT DOCUMENTS 3,595,621 A 7/1971 Andreatch
4,735,081 A * 4/1988 Luoma ................. G01N 29/036
73/24.06

(Continued)

FOREIGN PATENT DOCUMENTS

EP 0849587 A2 6/1998
EP 0849588 A2 6/1998
(Continued)

OTHER PUBLICATIONS

Smith, David, et al.; Making Sense of Taste; Scientific American Mar. 2001; https://cf.linnbenton.edu/mathsci/bio/wheatd/upload/making_sense_of_taste.pdf; pp. 32-39.
(Continued)

*Primary Examiner* — Gail Kaplan Verbitsky
(74) *Attorney, Agent, or Firm* — Bond, Schoeneck & King, PLLC; Jeffrey Powers (57) ABSTRACT

A multi-component fluid composition and concentration sensor system and method. The system can be configured with multiple sensing elements whereby each specifically responds to different combinations and concentrations of multiple fluid component mixtures. Because these responses can be captured and committed to a lookup table during an initial calibration sequence, subsequent measurements of unknown mixtures of the same gases will match known states found in the lookup table and the fluid concentrations can be deduced. The number of sensing elements with unique responses to the fluid mixtures should equal the number of unknown fluids that are active on the sensing (Continued)

surfaces, similar to how solving for multiple variables requires no fewer equations than there are unknowns, i.e. "3 equations and 3 variables." A reference surface can also be present in the fluid composition and concentration sensor so that the effects measured by the sensing surfaces can be determined against a relevant control that is not sensitive to the active fluids being measured.

12 Claims, 6 Drawing Sheets

(51) Int. Cl.
 *G01K 11/32* (2006.01)
 *G01N 27/407* (2006.01)
 *G01N 25/28* (2006.01)
 *G01N 27/16* (2006.01)
 *G01N 27/18* (2006.01)
 *G01N 33/00* (2006.01)

(52) U.S. Cl.
 CPC ............ *G01N 27/18* (2013.01); *G01N 27/407* (2013.01); *G01N 15/00* (2013.01); *G01N 33/0037* (2013.01); *G01N 33/0047* (2013.01); *G01N 33/0054* (2013.01)

(58) Field of Classification Search
 CPC ...... G01N 30/34; G01N 25/00; G01N 27/125; G01N 21/3504; G01N 2291/02809; G01K 13/02; G01K 13/00
 See application file for complete search history.

(56) References Cited

U.S. PATENT DOCUMENTS

| | | | | |
|---|---|---|---|---|
| 5,451,371 A * | 9/1995 | Zanini-Fisher | ........ | G01N 27/16 204/424 |
| 5,708,585 A | 1/1998 | Kushion | | |
| 6,009,742 A | 1/2000 | Balko | | |
| 6,060,991 A * | 5/2000 | Hsieh | ................ | G01N 33/0031 340/577 |
| 6,121,627 A * | 9/2000 | Tulip | ..................... | G01N 21/39 250/559.4 |
| 6,202,480 B1 * | 3/2001 | Mauze | ................... | G01N 25/64 374/109 |
| 6,242,263 B1 | 6/2001 | Faber et al. | | |
| 6,504,051 B1 * | 1/2003 | Miller, Jr. | ............. | C07C 51/265 562/404 |
| 6,516,656 B1 | 2/2003 | Jetter et al. | | |
| 6,549,276 B1 * | 4/2003 | Longtin | ............. | G01N 21/4133 356/128 |
| 6,912,907 B2 * | 7/2005 | Fujimoto | ................ | G01F 1/667 73/1.16 |
| 7,155,332 B2 * | 12/2006 | Yamada | .............. | F02D 41/0072 701/108 |
| 7,460,958 B2 * | 12/2008 | Walsh | ................ | G01N 33/0034 702/24 |
| 7,748,204 B2 | 7/2010 | Goman et al. | | |
| 7,763,208 B2 * | 7/2010 | Steichen | ............ | G01N 33/0031 422/88 |
| 8,820,050 B2 | 9/2014 | Dubkov et al. | | |
| 9,335,307 B2 * | 5/2016 | Wang | ..................... | G01N 30/86 |
| 9,590,169 B2 | 3/2017 | Ishida et al. | | |
| 10,018,613 B2 * | 7/2018 | Potyrailo | ............. | G01N 27/026 |
| 2001/0000852 A1 * | 5/2001 | Mauze | ................... | G01N 25/64 73/335.06 |
| 2003/0136193 A1 * | 7/2003 | Fujimoto | ................ | G01F 1/667 73/597 |
| 2004/0168504 A1 | 9/2004 | Eden | | |
| 2007/0202012 A1 * | 8/2007 | Steichen | ............ | G01N 33/0031 422/98 |
| 2008/0098799 A1 * | 5/2008 | Kirk | ....................... | G01N 25/20 73/25.01 |
| 2009/0039284 A1 | 2/2009 | Goto | | |
| 2013/0000278 A1 | 1/2013 | Dubkov | | |
| 2016/0238520 A1 * | 8/2016 | Broutin | ................... | G01N 33/04 |
| 2017/0227443 A1 * | 8/2017 | Hirano | ............... | G01N 15/1436 |
| 2018/0371520 A1 * | 12/2018 | Sharma | ..................... | C12Q 1/06 |
| 2019/0156600 A1 * | 5/2019 | Potyrailo | ............. | G07C 5/0816 |

FOREIGN PATENT DOCUMENTS

| | | |
|---|---|---|
| JP | S5770435 A | 4/1982 |
| JP | 06-501545 | 2/1994 |
| JP | 10-332674 | 12/1998 |
| JP | 2009294138 | 12/2009 |
| WO | 919971 A1 | 12/1991 |
| WO | 9732208 A1 | 9/1997 |
| WO | 2012164504 | 12/2012 |

OTHER PUBLICATIONS

Smith, David, et al.; Making Sense of Taste; http://tasteofchemistry.org/summer/r/docs/tastescientificamer.pdf; Scientific American, Inc. Copyright 2006; pp. 84-92.
EP Search Report dated Nov. 21, 2018 for Application No. 16812424.6; 11 pages.
JP office action for application No. Tokugan 2017-564346; dated Dec. 26, 2018; 9 pages.
International Preliminary Report on Patentability for International Application No. PCT/US2016/037848 International filing date Jun. 16, 2016, pp. 1-7.
International Search Report for International Application No. PCT/US2016/037848, International Filing Date Jun. 16, 2016 pp. 1-11.
JP office action for application No. Tokugan 2017-564346; dated Mar. 6, 2020; 5 pages.

* cited by examiner

SYSTEM AND METHOD FOR DETERMINING ONE OR MORE FLUID CONCENTRATIONS IN A FLUID STREAM

RELATED APPLICATION DATA

This application claims priority to International Application No. PCT/US2016/037848 filed Jun. 16, 2016, which claims priority to U.S. Provisional application Ser. 62/180,099 filed Jun. 16, 2015, the subject matter of each of which is incorporated herein by reference in its entirety.

FIELD OF THE INVENTION

The present disclosure relates generally to systems and methods for in situ fluid composition and concentration detection/measurements.

BACKGROUND

Various conventional forms of NOx sensors are known. Current state of the art compact mass-produced NOx sensors, as employed in the large IC engine and transportation industry, are extremely limited in variety, and are all based on solid-state electrochemical diffusion techniques that are, in turn, based on the original solid-state electrochemical oxygen sensor—a four-decade-old technology.

Since the following two patents issued—U.S. Pat. No. 4,770,760 ("Reduction, oxygen pumping and sensing cells, exhaust gases") and U.S. Pat. No. 4,927,517 ("NOx sensor having catalyst for decomposing NOx")—no significant market competition has emerged that supplants the current technology of mass-produced NOx sensors, consisting of diffusion based electrochemical detection methods. As a historical note, the aforementioned NOx sensors were, in turn, based on lambda (oxygen) sensors, specifically Robert Bosch G.M.B.H's 1976 patent U.S. Pat. No. 3,978,006 ("Methods for producing oxygen-sensing element, particularly for use with internal combustion engine exhaust emission analysis").

Related art that has not yet achieved mass production or market acceptance, namely Nextech Materials, Ltd., with their patent application WO2013134738 A1, employs a method that bypasses the sequential diffusion steps and oxygen sensor detection techniques. Nextech accomplishes this by directly reducing NOx into oxygen ions that are subsequently injected into the amperometric device. While this is advancement over prior art, it is still a derivation of existing and extant techniques. In fact, it benefits from existing technology with oxygen migration through a solid electrolyte which in turn yields an amperometric response to oxygen ions which are electrically pumped through a specific material and subsequently measured, thereby inferring NOx concentration through an indirect means. But by doing this, Nextech Materials has overcome some (but not all) of the time delays inherent to systems based off the classic oxygen sensor.

In other mass produced related art, which represents virtually all of existing in situ NOx sensors for internal combustion applications, the concentration of NOx contained in a measurement gas (i.e. exhaust stream) is determined using primary and secondary electrochemical detecting elements, each of which includes an oxygen-pumping cell and an oxygen-sensing cell. Each of the pumping and sensing cells of the first and second detecting elements consists of a solid electrolyte and a pair of electrodes. At least one of the electrodes of the oxygen pumping and sensing cells of the second detecting elements which are exposed to the introduced measurement gas is used as a catalytic electrode which is manufactured with a catalyst, such as rhodium, for reducing the nitrogen oxides contained in the measurement gas. Oxygen is a reduction byproduct of NOx. Therefore the second detecting element (electrochemical oxygen sensor) can detect the oxygen partial pressure of the measurement gas generated as a result of the nitrogen oxides being reduced by the catalyst of the catalytic electrode. The NOx concentration is determined, based on a difference between two outputs of the first and second detecting elements which represent the oxygen partial pressures of respective portions of the measurement gas detected by the first and second detecting elements. The exact method of oxygen concentration measurement using this method can employ potentiometric mixed potential, impedance-based or, as mentioned with Nextech, amperometric sensor types.

The main problem with the conventional art stems primarily from the delays in measurement inherent to the design. Specifically, since mass produced NOx sensors are based off lambda (oxygen) sensors, each individual (and sequential) measurement within the multi-chambered sensor can take up to half a second. This is because the measurements take place in two separate chambers in the sensor, and the exhaust gases flow sequentially through one and then into the other. Gases flow from the exhaust stream through a diffusion barrier to reach the first chamber, which "pumps" the free oxygen out using a Nernst cell (simple oxygen sensor). The electric current for operating this first Nernst cell is used to measure exhaust oxygen content (lambda). With the free oxygen removed, the NOx is then left to migrate through another diffusion barrier and into the second measurement chamber. At this point, the NOx molecules encounter a catalytic element, which breaks them into nitrogen and oxygen gases. A second Nernst cell is then used to pump the newly generated oxygen out of the chamber, and this electric current is used to calculate the NOx levels in the exhaust. The residual nitrogen gases then flow out an exit port in the second measurement chamber. When combined with the diffusion barriers found within existing NOx sensor designs the overall measurement delay can be on the order of seconds. This process duration can be further increased as the system ages. While Nextech advanced the art, there is still a diffusion process of oxygen ions through a crystal substrate that accounts for their 50 millisecond response time.

Accordingly, there is a need in the art for improved devices and methods for in situ fluid composition and concentration detection/measurements including a mechanism or structural configuration to eliminate delays in such detection/measurements, and to provide an overall indication/determination of the efficiency of catalytic devices such as catalytic converters of internal combustion engines at a particular point in time.

Description of the Related Art Section Disclaimer: To the extent that specific patents/publications/products/systems are discussed above in this Background Section or elsewhere in this application, these discussions should not be taken as an admission that the discussed patents/publications/products/systems are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products/systems are discussed above in this Background Section and/or throughout the application, the descriptions/disclosures of which are all hereby incorporated by reference into this document in their respective entirety(ies).

SUMMARY OF THE INVENTION

The present disclosure is directed to inventive systems and methods for determining the concentration of at least one fluid component in a fluid stream during a first time period. Various embodiments and implementations herein are directed to a system that includes a multi-component fluid composition and concentration sensor system. The system can be configured with at least one and preferably multiple sensing elements whereby each specifically responds to different combinations and concentrations of multiple fluid component mixtures. These responses can be captured and committed to a lookup table/stored library during an initial calibration sequence, subsequent measurements of unknown concentrations of mixtures of the same gases will match known states found in the lookup table and the fluid concentrations can be deduced. The number of sensing elements with unique responses to the fluid mixtures should equal the number of unknown fluid components that are active on the sensing surfaces, similar to how solving for multiple variables requires no fewer equations than there are unknowns, i.e. "3 equations and 3 variables." A reference surface is also present in the fluid composition and concentration sensor so that the effects measured by the sensing surfaces can be determined against a relevant control that is not sensitive to the active fluids being measured. The multi-component fluid composition and concentration sensor system, in the case of a NOx sensor or related art, can work with other sensors on the IC engine platform, such as oxygen sensor, fuel flow, and mass flow, specifically when such parameters affect the fluid composition and concentration sensor's output. When this is the case the values from these external sensor values can be included in the lookup table during part of the initial device calibration process.

According to other embodiments and implementations, pertinent information/messages/alerts regarding the concentration of catalyzable fluid components in a fluid stream can be provided to users of the system described herein on a user interface of a computing device wirelessly or via a wired connection.

Generally, in one aspect, a system is provided for determining the concentration of at least one fluid component in a fluid stream during a first time period, the system including: a housing defining an interior section with a fluid inlet port and a fluid exit port, the housing being configured to accommodate the flow of a fluid stream from the fluid inlet port to the fluid exit port; a reference sensor substrate positioned within the housing, connected to a reference sensor and configured to measure a reference temperature value, a reference optical value, or a reference morphological value of the interior of the housing during a first time period; a first active sensor positioned within the housing and configured to measure a first deviation of temperature value, a first deviation of optical value, or a first deviation of morphological value caused by presence or activity of the first fluid component in the fluid stream within the housing; and a processor in communication with the first active sensor and the reference sensor and configured to determine the concentration of the first fluid component in the fluid stream during the first time period by: comparing the first deviation of temperature value, first deviation of optical value or first deviation of morphological value to a stored library of a plurality of predetermined deviation temperature, optical or morphological values for the first fluid component, and matching the first deviation of temperature, optical or morphological value to an equivalent predetermined deviation temperature, optical or morphological value. A corresponding method is also provided that include providing this system, measuring the reference temperature, optical, or morphological values; measuring the respective deviation values caused by the presence or activity of each of the fluid components, and determining the concentration of each fluid component based on the respective deviation values.

Generally, in another aspect, a system is provided for determining the concentration of at least one fluid component in a fluid stream during a first time period, the system comprising: a housing defining an interior section with a fluid inlet port and a fluid exit port, the housing being configured to accommodate the flow of a fluid stream from the fluid inlet port to the fluid exit port; a non-catalytic reference sensor substrate positioned within the housing, connected to a reference temperature sensor and configured to measure an absolute temperature value of the interior of the housing during a first time period; a first active catalyst sensor positioned within the housing and configured to catalyze a catalyzable first fluid component in the fluid stream during the first time period when the fluid stream contacts a surface of the first active catalyst sensor, wherein the catalysis of the catalyzable first fluid component results in a first deviation of temperature value at the surface of the first active catalyst sensor from the absolute temperature value; a first temperature sensor connected to the first active catalyst sensor and configured to measure the first deviation of temperature value; and a processor in communication with the first temperature sensor and the reference temperature sensor and configured to determine the concentration of the first fluid component in the fluid stream during the first time period by: comparing the first deviation of temperature value to a stored library of a plurality of predetermined deviation temperature values for the first fluid component being catalyzed by the first active catalyst sensor, and matching the first deviation of temperature value to an equivalent predetermined deviation temperature value.

Generally, in another aspect, a method is provided for determining the concentration of at least one fluid component in a fluid stream during a first time period, the method including the steps of: providing a system comprising: a housing defining an interior section with a fluid inlet port and a fluid exit port; a non-catalytic reference sensor substrate positioned within the housing and connected to a reference temperature sensor; a first active catalyst sensor positioned within the housing; a first temperature sensor connected to the first active catalyst sensor; and a processor in communication with the first temperature sensor; providing a fluid stream through the interior section of the housing from the fluid inlet port to the fluid exit port; measuring, with the non-catalytic reference sensor substrate, an absolute temperature value of the interior of the housing during a first time period; catalyzing, with the first active catalyst sensor, a catalyzable first fluid component in the fluid stream during the first time period when the fluid stream contacts a surface of the first active catalyst sensor, wherein the catalysis of the catalyzable first fluid component results in a first deviation of temperature value at the surface of the first active catalyst sensor from the absolute temperature value; measuring, with the first temperature sensor, the first deviation of temperature value; determining, with the processor, the concentration of the first fluid component in the fluid stream during the first time period by: comparing the first deviation of temperature value to a stored library of a plurality of predetermined deviation temperature values for the first fluid component being catalyzed by the first active catalyst sensor, and matching the first deviation of temperature value to an equivalent predetermined deviation temperature value.

As used herein for purposes of the present disclosure, the term "processor" is used generally to describe an apparatus relating to the operation of at least a portion of the system or method described herein. A processor can be implemented in numerous ways (e.g., such as with dedicated hardware) to perform various functions/method steps discussed herein. The processor can employ one or more microprocessors that may be programmed using software to perform various functions/method steps discussed herein. A processor may be associated with one or more storage media or memory (which may be portable). In some implementations, the storage media may be encoded with one or more programs that, when executed on one or more processors and/or controllers, can perform at least some of the functions/method steps discussed herein. The term "computing device" as used herein may be a general purpose computer, a mobile device, smart phone, tablet (as well as any other fixed or mobile computerized device comprising a processor and a network connection and capable of communicating with the other components via a wired or wireless connection), a custom dedicated computing device, or any other computing device capable of storing—per a memory—and executing—per a processor—the algorithm(s)/program(s)/software described herein (as should be understood by a person of skill in the art in conjunction with a review of this disclosure). A computing device may store and execute a mobile or other application.

The data transmission, communication, and any control signals between computing devices can be sent and received pursuant to wired or wireless communication. The wireless communication/transmission can be over a network, which can be any suitable wired or wireless network capable of transmitting communication, including but not limited to a telephone network, Internet, Intranet, local area network, Ethernet, online communication, offline communications, wireless communications and/or similar communications means. The wireless transmission can be accomplished through any wireless protocol/technology, including, but not limited to, ZigBee standards-based protocol, Bluetooth technology, and/or Wi-Fi technology. Further, this data can be encrypted as needed based on the sensitivity of the data, for example.

The term "attached" as used herein can refer to directly attached or indirectly attached.

The term "connected" as used herein can refer to directly connected or indirectly connected.

The "point in time" or "time periods" noted herein can be an instantons point in time, or can be an average of values over any period of time based on samplings taken over such period of time in any type of interval—e.g., every millisecond, every second, every minute, every 15 minutes, or every hour, depending on how often the temperature sensors are queried/interrogated.

The details of one or more embodiments are described below and in the accompanying drawings. Other objects and advantages of the present invention will in part be obvious, and in part appear hereinafter.

BRIEF DESCRIPTION OF THE DRAWINGS

The present invention will be more fully understood and appreciated by reading the following Detailed Description in conjunction with the accompanying drawings, in which.

DETAILED DESCRIPTION OF EMBODIMENTS

The following detailed description of certain embodiments should not be used to limit the scope of the claimed invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

The present disclosure is directed to inventive systems and methods for determining the concentration of at least one fluid component in a fluid stream during a first time period based on a thermal, optical and/or morphological change as measured against a reference measurement. More generally, Applicant has recognized and appreciated that any fluid, including liquid or gas, that has the capability of imparting thermal, optical, or morphological change on a solid is a candidate for detection using the embodiments disclosed herein, and that it would be beneficial to measure the concentration of catalyzable fluid components in a fluid stream via endothermic/exothermic catalytic reactions. An example of a thermal change would be the thermal effect imparted by an oxidizing or reducing fluid (e.g., CO or NOx) across a relevant catalyst.

Thermal changes and trend events can be measured with extreme precision using various methods, including but not limited to fiber optic sensing such as fiber Bragg gratings (FBG) or multicore fiber technology; or thermocouples. Examples of exothermic events involving a liquid across a solid catalyst should be understood and appreciated by those of skill in the art in conjunction with a review of this disclosure. An example of an optical change can be a fluorescence reaction. Optical events can be monitored with the help of light collectors, waveguides and/or fiber optics. An example of morphological change is the reversible crystal structure change in a metal hydride undergoes when it takes on and gives up hydrogen. Morphological changes that generate measurable strain values and can be monitored using sensitive strain gauges including strain sensitive FBGs, multicore fiber optics, or conventional strain gauges.

A non-limiting embodiment of the present disclosure can be implemented as in-situ internal combustion (IC) engine exhaust monitoring, including (but not limited to) NOx (consisting of nitric oxide, NO; and nitrogen dioxide, NO2) gas sensors. As described further below in conjunction with the Figures and the NOx sensor embodiment, the embodiment can relate to a series of manufactured surfaces inside a device housing, each with a unique/different catalyst that responds to IC exhaust gases with a different change in temperature ($\Delta T$) according to the catalyst used and the precise makeup of the exhaust gas. The catalytic surfaces can each have individually unique sensitivities to nitric oxide (NOx), carbon monoxide (CO), and unburned hydrocarbons (HC) concentrations; these response patterns can also vary divergently with respect to one another as a function of varying % gas composition. This variation and mathematical divergence of signal response can also extend to different temperature regimes, and also other regimes such as overall oxygen content and mass flow. Each catalytic surface can respond uniquely (different $\Delta T$) in a given mixture of exhaust gases. There can also be a reference surface that is non-catalytic so that absolute temperature of the system absent any catalytic effects can be determined.

In a given application (diesel exhaust, gasoline exhaust, etc.), an embodiment of the present disclosure is initially calibrated and the thermal states of the catalytic surfaces are recorded in known concentrations of known mixtures of exhaust gases to yield a response map of predetermined values that are stored in a computing device memory as a lookup table or "library" (e.g., a particular deviation/variation from the absolute temperature/reference temperature recorded by a reference sensor at each surfaces of three different catalyst sensors due to the catalysis of known concentrations of NOx, CO and uncombusted hydrocarbons in a fluid flow at a particular point in time or time period). The calibration process can be tailored to the expected end-use of the invention, and may also utilize other variables like oxygen content and mass flow from secondary sensors whose values are available in the sensor network.

Device calibration can initially be performed using a secondary measurement device of known calibration. The $\Delta T$ calibration response map of the invention can then be assigned to a lookup table (or similar approach) for subsequent IC exhaust gas concentration measurements without the secondary device of known calibration because now the reference lookup table or library has been created. This is because the temperatures of all the parts of the sensor will always be the same and will always be repeatable in a given gas mixture environment at a given system temperature. The resulting calibration response map can have as many axes as there are expected gas components (or other variables, such as mass flow or background temperature) to be measured. Each response map coordinate value (i.e. u, v, w, x, y, z) is the catalytic sensing surface value minus the reference temperature value from the reference surface measured by the reference sensor. Furthermore, sensor data and other parameters (oxygen, RPM, fuel consumption) already being measured and captured within the IC engine control system (i.e. engine computer and sensor network), can be leveraged to further improve the accuracy of the proposed embodiment by incorporating such information into the calibration map (as should be understood by those of skill in the art in conjunction with a review of this disclosure).

Advantages of embodiments (as briefly detailed above, and described below and shown in the accompanying Figures) are illustrated by the following Exemplary System, Methods and Uses description. However, the particular components, uses, functionalities and amounts thereof recited in this description, as well as other conditions and details, are to be interpreted to apply broadly in the art and should not be construed to unduly restrict or limit the invention in any way. In particular, the NOx related sensor embodiment with its calibration response map represents only one example of how the design principles described herein and can be applied to many different fluid species across a wide variety of measurable thermal, optical, or morphological changes.

Exemplary Methods and Uses

Figure 1A:
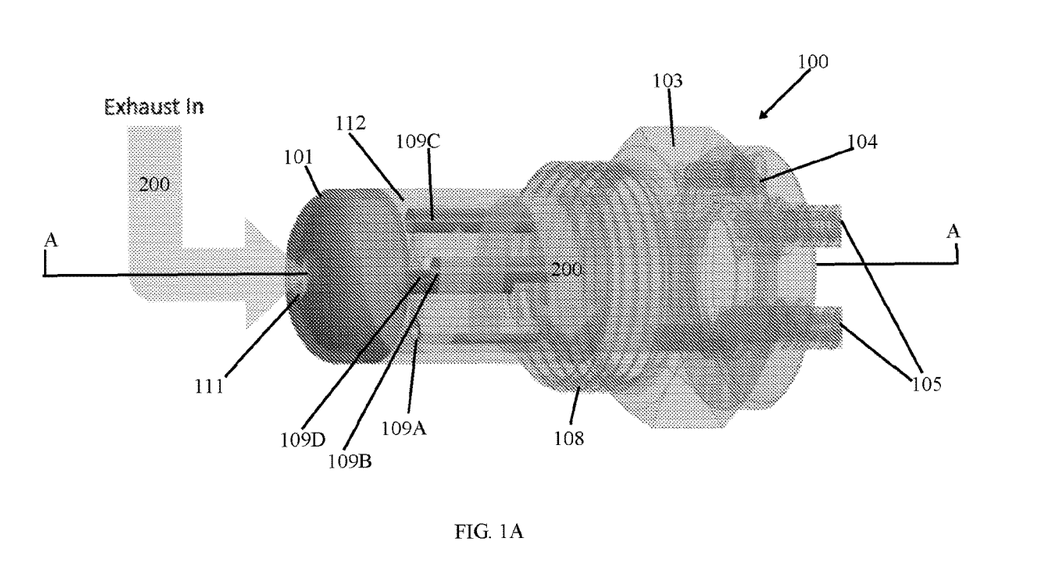
FIG. 1A is a perspective view three dimensional schematic representation of a system in an assembled state configured and/or programmed to determine the concentration of at least one fluid component in a fluid stream during a first time period, according to an embodiment.
Figure 1B:
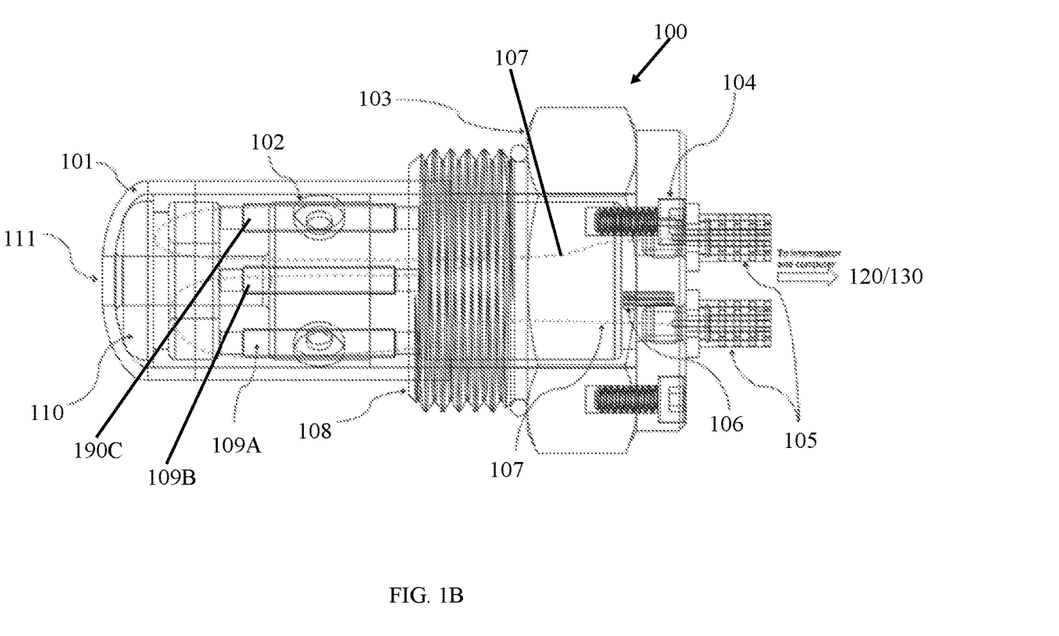
FIG. 1B is a cross-sectional view schematic representation of the system taken along A-A of FIG. 1A, according to an embodiment.

The system disclosed herein, using the NOx sensor as one embodiment, includes an in-situ and/or inline sensor(s) for measurement of NOx in an IC engine exhaust gas flow or stream (but is not limited to an IC application). As described herein, an embodiment of the system described herein can also measure uncombusted hydrocarbons and carbon monoxide, for example, as part of the method to determine NOx concentration. In one embodiment, the system is configured to be mounted downstream of the IC engine exhaust manifold, for example. The system can be designed such that power is not required for operation, specifically if and when cold measurement error can be tolerated. If it is required that the system needs to provide high levels of accuracy at engine startup (cold/ambient temperatures) then heating elements may be optionally employed. An embodiment of the system is preferably constructed of materials that can withstand temperatures up to 1000° C. The outer housing 101 (FIG. 1) is preferably made of a durable yet relatively inert material such as stainless steel meant to withstand handling, installation with common tools, and/or harsh environments including high temperatures. Besides high temperatures, the entire assembly/system can be able to withstand other phenomena such as thermal cycle over many years, vibration and jolts, or to be able to withstand various chemical environments which are anticipated with alternate material selections as the application demands.

Referring to FIG. 1A, in one embodiment, is a perspective view three dimensional schematic representation of a system 100 in an assembled state configured and/or programmed to determine the concentration of at least one fluid component in a fluid stream during a first time period. FIG. 1B is a cross-sectional view schematic representation of system 100 taken along A-A of FIG. 1A. System 100 may include one or more of the following components: a housing 101, exhaust ports 102, sensor bolt fitting 103, assembly screws 104, optical communication ports 105, positioning pin 106, multi sensor fiber optic 107A-D (shown in FIG. 3), sensor mounting threading 108, sensor element substrates 109A-D (preferably thermally isolated from one another), ceramic sensor element housing 110, and fluid inlet 111. Fluid stream 200 containing the three fluid components desired to be measured—NOx, CO, and uncombusted hydrocarbons (HC)—is shown flowing through the inlet 111 and in and around sensor element substrates 109A-D. System 100 may be preferentially mounted downstream of the IC engine (not shown) in a location that ensures proper flow of exhaust gas through the device housing 101, such that the operating temperature of the sensing element substrates 109A-D occurs in such a range that guarantees optimal catalytic conversion of said exhaust gas fluid components. The optimizing of the positioning and operating temperature of the sensing device occurs during the design phase for any given application, since the combustion flow and temperature specifics are unique to each application (as should be understood and appreciated by those of skill in the art in conjunction with a review of this disclosure). In most preferred cases, the location of the sensor will be selected such that the optimized flow and temperature values for that location yields optimum sensing element performance.

The housing 101 can be fabricated of stainless steel or other such material that allows the device to function in harsh environments. The lower limit of the size of the housing 101 is only constrained by how small the sensing elements 109A-D can be constructed while still maintaining the ability to withstand the operating environment, with the current lower limits being the size of fiber optic sensing elements (250 μm diameter, 15 mm length), packaged in such a manner that can withstand shock, vibration, thermal cycle, and gas flow velocities associated with an internal combustion engine; notionally between 1 and 2 cm$^3$ as a lower limit with existing technology. Fluids exiting the system 100 do so through two or more exhaust ports 102 in the side of the housing 101 (which could be placed elsewhere as may be convenient). These fluid ports are also present in the ceramic sensor element housing 110. The device may optionally bear a bolt fitting 103 of any of various sizes to allow for the invention to be properly fitted in a useful environment, such as inside the exhaust zone of a turbine engine, or exhaust manifold of an IC engine (as should be appreciated by those of skill in the art in conjunction with a review of this disclosure). Assembly screws 104 mechanically join the ceramic sensor element housing 110 (with relatively low thermal conductivity, within which the sensor element substrates are mounted so as to avoid transfer/cross contamination of thermal energy from one sensor element substrate to another) to the sensor housing 101 Sensor housing 101 shields the sensor element housing 110 from mechanical actions such as handling, placement, tightening, and any foreign object damage that may be part of the exhaust stream; while also insulating the sensor element housing from temperature variations associated with the location of the exhaust sensor. Optical communication ports 105 optionally provide connections for fiber optic line to travel outside the device to a laser energy source/interrogator (see ref no. 120 in FIG. 3). Note, as discussed elsewhere in this disclosure, the embodiment of the system 100 is not limited to fiber optic methods of temperature determination or communication. Positioning pin 106 allows the ceramic sensor element housing 110 to be properly positioned in sensor housing 101 prior to tightening the assembly screws 104. The multi-sensor fiber optic 107, in the case of fiber-optic data communication, has one sensor region (for example fiber-Bragg-grating or multicore fiber optic, RTDs, conventional thermocouples) per sensing element. This allows one single fiber with multiple contiguous sensor regions to monitor all sensing elements on the same channel. Sensor mount threading 108 allows the device to be screwed into the target application.

Sensor element substrates 109A-C are shown as three tubes, each of which is coated with a different catalyst (e.g., a transition metal), or transition metal chalcogen (oxide, sulfide, selenide, etc.), on the outer surface thereof (but can be on the inner surface), to determine the concentration of the three fluid components. The reference sensor element 109D is also shown as a tube, but us not coated with a catalyst, as it will be assist in the measurement of the absolute temperature/reference temperature of the interior of the housing at a particular time frame during fluid flow through the housing. The sensor element substrates 109A-D are constructed of a low CTE material with high TC such as tantalum (Ta) metal (Ta CTE=6.5 μm/m° C., Ta TC=57 W/mK), or other such non-catalytic materials exhibiting similar properties. In turn they are all mounted in a ceramic sensing element housing 110 with low CTE. Low CTE relates to the properties of optical fibers constructed of silica, and the desire to match this CTE so as to avoid imparting any mechanical stretching or bending associated with a CTE mismatch. The CTE of fused silica is typically under 1 μm/m° C. Such a mismatch can lead to a reduction in optical fiber signal quality, or otherwise additional mechanical action that can lead to optical fiber damage, degradation, or false signal generation. Because of this it is advantageous to directly place any optical fiber sensors in housings constructed of low CTE materials such as other ceramics which have CTE values of 9 μm/m° C. or less such as alumina (8.1 μm/m° C.), aluminum nitride (5.1 μm/m° C.), mica (3 μm/m° C.), or silica. Depending on whether it is advantageous to thermally isolate sensing element signals or transmit heat through a sensing element it may be desirable to employ either low or high TC materials. Optical fiber silica itself has a low TC, typically less than 2 W/mK. Common ceramics such as alumina only have a TC of 30 W/mK. Metals such as aluminum have a CT of over 200 W/mK, but aluminum also has a high CTE of over 22 μm/m° C., making it undesirable to use for a fiber optic housing fiber since it may be important to minimize unwanted component expansion, as described above. Aluminum nitride is an unusual ceramic in that it has a CT that approaches aluminum metal, or 180 W/mK. Aluminum nitride, like tantalum, is advantageous when low CTE combined with high CT is desired. Given the temperature swings of the system 100 as used in IC applications, the CTE values of the system can be carefully matched to avoid damage (as should be appreciated by those of skill in the art in conjunction with a review of this disclosure). Because the internal sensing elements exhibit a thermal response that is a function of the concentration of the measured gases (NOx, CO, HC), these sensor element substrates 109A-D could possibly be tubular shaped (as discussed above and shown in the Figures), which allows for the measurement gas to flow around them and allowing for the temperature of each tube to be discerned from the inside (or outside if the catalyst is coated on the inside) using any number of various methods. The sensor element substrates 109A-D can also be of any shape that suits the measurement requirements and needs, with various 2D, various 1D, or even point detectors possible. Various arrangements and combinations of the aforementioned are possible as it suits the need of the design, including coating the temperature sensor itself in place of and in the position of the sensor element substrates 109A-C within the housing and without any additional sensor element substrate.

As described herein, each of the sensor element substrates 109A-C (sensor substrate elements other than the reference sensor element substrate) can be coated with a different/unique catalytic material and/or reference materials (and various mixtures thereof). The sensing elements of an embodiment described above are preferentially coated with any of several different materials, specifically including catalytic materials and also reference materials. Catalytic materials include, but are not limited to, copper (Cu), platinum (Pt), palladium (Pd), rhodium (Rh), silver (Ag), gold (Au), ruthenium (Ru), iridium (Ir), vanadium oxide (V2O5), and other transition metals, as well as alloys or mixtures thereof. In other embodiments, besides a NOx sensor, it's possible that non-catalytic materials may be utilized that exhibit useful and repeatable crystallographic transitions that leave a measurable thermal signature or even measurable strain or possibly optical signatures, so the active sensing elements are not necessarily catalytic. That said, this disclosure uses the term "catalytic" even though it's possible to measure any fluid within a multi-component composition that generates any morphological/chemical activity yielding a thermal, optical, strain, or some other measurable event. In the event of a strain event, the distortion of the sensing elements could be used instead of the change in temperature. In the event of liquid instead of a gas, and the effect results in a crystallographic/morphological strain, the liquid flow pressure against the sensor should be subtracted out using a designated reference to accurately measure the physio-chemical effects. In the event of an optical event, the light generation can be monitored and is what establishes the sensor signal, with ambient light (if any) being accounted for with a reference. There is no restriction on how the effect can be measured, or what environmental variables would need to be accounted for.

Reference coating material should have qualities not too dissimilar from the sensor coating materials, such as higher melting point, good TC, and higher density. Reference coating materials, such as tungsten (being an inert (non-catalytic) material), approximate the physical presence of a notional catalytic coating by providing a finite thickness through which heat must flow and/or a layer that adds mass or volume to the system; but such a reference coating does not itself exhibit any catalytic properties. Such a coating will provide a better reference signal, since it is advantageous to construct the reference in such a manner that it provides the most accurate system temperature used as the reference; best approximating the physical construction of the active sensors insofar as heat flow, mass, or any mechanical effects such as vibration that would impact all the temperature sensor signals and how they are constructed and implemented as a fluid sensor.

Any sensing or reference materials (i.e. catalysts, blanks) can be deposited on the outside of the sensor element substrates 109A-C in any of several ways, including but not limited to electroplate, chemical vapor deposition (CVD), physical vapor deposition (PVD), sputtering, sol-gel deposition, or as pure powders adhered in turn to an intermediate thin cementing layer. Such a cementing layer, besides being as thin as possible, can also exhibit as high a TC as is possible so as to maximize response time and minimize thermal losses. The CTE of the various materials employed can reflect the end use of the invention; large thermal cycles of the invention should not lead to self-destruction of the unit.

The quantity of sensing elements/element substrates is preferably a minimum of 2 (1 catalytic, 1 reference) for use measuring a single-component catalytically active fluid stream. In this case, the concentration of that species is simply a mathematical function of the temperature of the one sensing element, although that calculated response may also vary with temperature or oxygen concentration or other inputs with data streams available on the network, if any (variable of which can be considered in the calculations performed by the processor 130 in FIG. 3). For every additional fluid component present that undergoes a catalytic reaction, there should preferably be a matching number of unique/different sensing elements present in order to quantify each component's concentration. There is preferably no variation to this rule, unless there exists a pre-defined relationship between a molecular species and its dimer, as the dimer would not count as a distinct species (or variable). The relationship is similar to multiple variables being solved with multiple equations. Also, it is not possible to measure the concentration of a species that does not undergo catalytic reaction via a temperature change per a catalytic reaction, such as nitrogen (N2) or argon (Ar). Correspondingly, the presence of N2, Ar, and other such gases can effectively be ignored, and they can normally be disregarded in these use-cases since such fluid components are inert.

A typical NOx sensor system of an embodiment can have four or five sensing elements. In most cases four will be sufficient for measuring NOx in an environment that, besides NOx, also contains CO and HC. In cases where ammonia (NH3) is also present, for example, a fifth sensing element would need to be present because NH3 is catalytically active and would need its own equation because it's the fourth unknown in the system of equations (i.e., algebraic catalytic equations each with unknown variables=concentrations of a particular catalyzable fluid component to undergo a catalytic reaction). In this case, the NH3 concentration at that point in the combustion stream would be calculated as well, allowing for any ammonia slip to be accounted for; in addition to CO, HC, and NOx (and, allowing for a determination of the efficiency of the connected system to be determined). Besides NOx, all active gases present in the stream will necessarily have their concentrations quantified as a result of the method of NOx concentration determination. The least accurate concentration calculation represents the overall inaccuracy of the system.

Figure 2:
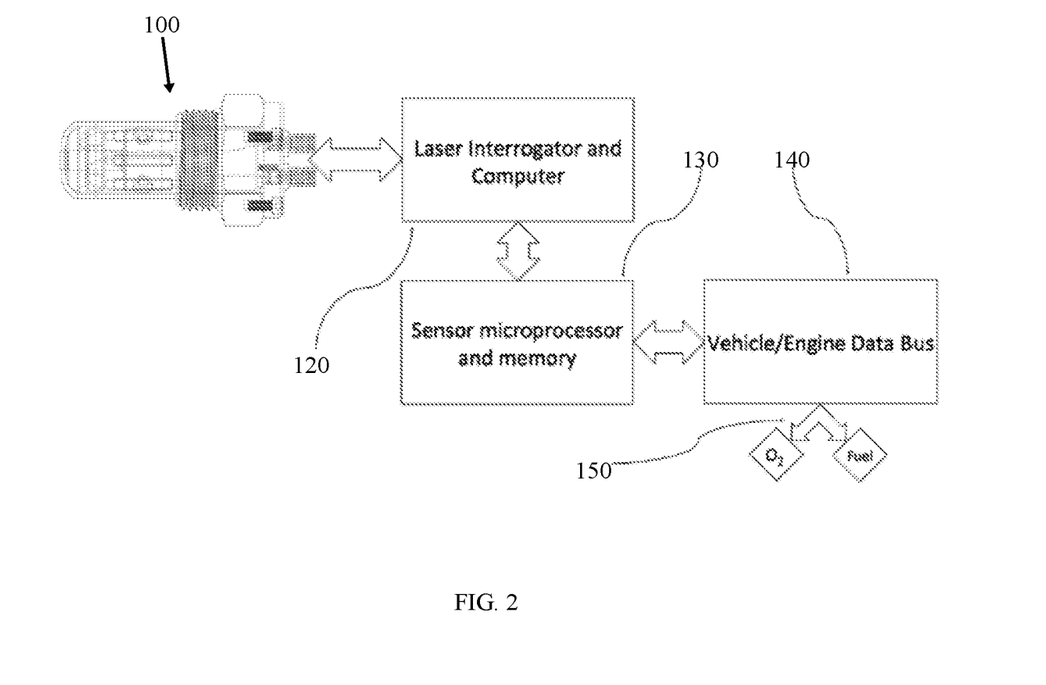
FIG. 2 is a cross-sectional view schematic representation of the system taken along A-A as shown in FIG. 1B, and is connected to an interrogator and computing device, a computing device with sensor processor/microprocessor 130, and a vehicle/engine data bus, according to an embodiment.

Referring to FIG. 2, in one embodiment, is a cross-sectional view schematic representation of system 100 taken along A-A of as shown in FIG. 1B, and is connected to an interrogator and computing device 120, a computing device with sensor processor/microprocessor 130, and a vehicle/engine data bus 140. In brief, FIG. 2 shows how system 100 works with related equipment, sensors, and systems in a relevant environment such as an IC-powered vehicle with a modern system-level control system and associated data bus 140. Interrogator and computing device (e.g., from Micron Opics) 120 is configured, connected and/or programmed to interact with/query fiber sensing elements 107 connected to the sensing element substrates 109A-D to obtain readings indicative of temperature readings (as should be appreciated by those of skill in the art in conjunction with a review of this disclosure). Interrogator and computing device 120 can be communicatively coupled to computing device with sensor processor/microprocessor 130, or can be part of the same computing device. Each of the computing devices 120/130 can implement programs based on temperature sensor input gathered inside the housing of the system 100 (e.g., at sensor element substrates 109A-D). Each computing device 120/130 may also cooperate (communicate, receive or provide instructions or other data via a wireless or wired connection) with one another or other separate computing devices running a particular application for analysis, calculations, determinations, and display of pertinent information to a user (concentration outcomes as described herein) at a user interface (not shown) physically separated from computing device 110.

For example, a user using computing device 120 can instruct the interrogator to send data transmission, control or communication signals to the fiber optic sensors 107 (optically interrogate) to obtain various readings that can be translated into a temperature reading, and to computing device 130 processor/memory in order to instruct the computing devices 120/130 to perform any of the functionalities described herein (as should be understood by a person of skill in the art in conjunction with a review of this disclosure). Computing device 130 can include a microprocessor/processor and sufficient memory to store and provide access to a lookup table/library (as described above) for proper device functioning as described herein; where "microprocessor" is not a limiting term and can include one or more microcontrollers, microcomputers, PLCs, CPUs, processors, integrated circuits, field programmable gate array, or any other programmable circuit or combination of circuits. Stated differently, optical interrogation can be accomplished with computing device 120 (including the optical interrogator), which is communicatively coupled to computing device 130, which is programmed/configured to perform the calibrated output (look up table to determine concentrations of various catalyzable fluid components based on temperature deviations in view of catalytic activity at a surface of a particular catalyst).

Computing devices 120/130 can also be configured/programmed/connected to interface and work with the vehicle software/hardware data/communication bus 140 and associated protocols to provide sensor input on the measured parameters, such as NOx content and other gas concentration information as well as temperature of the exhaust stream at that point. Tertiary sensors 150 may provide additional information, values and controlled variables to assist in the functioning of the system 100, that including expected values for lookup table entries and calculations.

Figure 3:
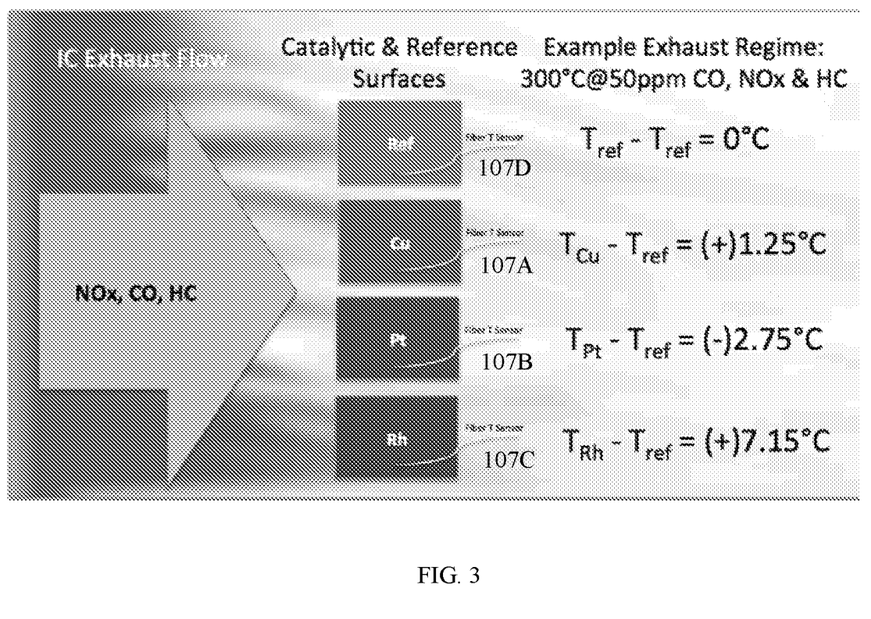
FIG. 3 a flow chart generally showing IC Exhaust flow containing three catalyzable fluid components (NOx, CO, and HC) over three different catalytic surfaces (Cu, Pt, and Rh) and over a reference surface, according to an embodiment.

Referring to FIG. 3, according to an embodiment, is a flow chart generally showing IC Exhaust flow containing three catalyzable fluid components (NOx, CO, and HC) over three different catalytic surfaces (Cu, Pt, and Rh) and over a reference surface. Each of the surfaces are attached to a fiber optic sensor 107A-D (which are connected to an interrogator and computing devices 120/130, as shown in FIG. 2), which senses the differences in temperature at each surface. Four equations are shown, one for the reference (which=0 deviation temperature value, and is the control), and three others—one for each catalyst—which show deviations/variations in temperature from the reference temperature. These temperatures can then be compared to a library of temperature values to obtain the concentration of NOx, CO, and HC (which is shown in this example as 50 ppm).

The fiber optic sensor shown in these examples can relate to multicore photonics, which use extremely sensitive fiber optic based temperature sensors to monitor differences in the thermal activity found at the surface of active catalysts in the process of catalytic reduction and/or oxidation of the exhaust stream components. Each catalyst responds uniquely to the presence of the three gases shown in FIG. 3, with the temperatures changing differently as concentration varies over time. With as many catalysts present as there are unknown fluid component concentrations to be measured, a calculation of the presence of and concentration of NOx, CO and unburned hydrocarbons using a lookup table and solving for the unknowns can be performed. As noted, the reference T surface is not responsive to these species so as to provide a background temperature. The lookup table can be created during the calibration process for subsequent species value determinations.

Figure 4:
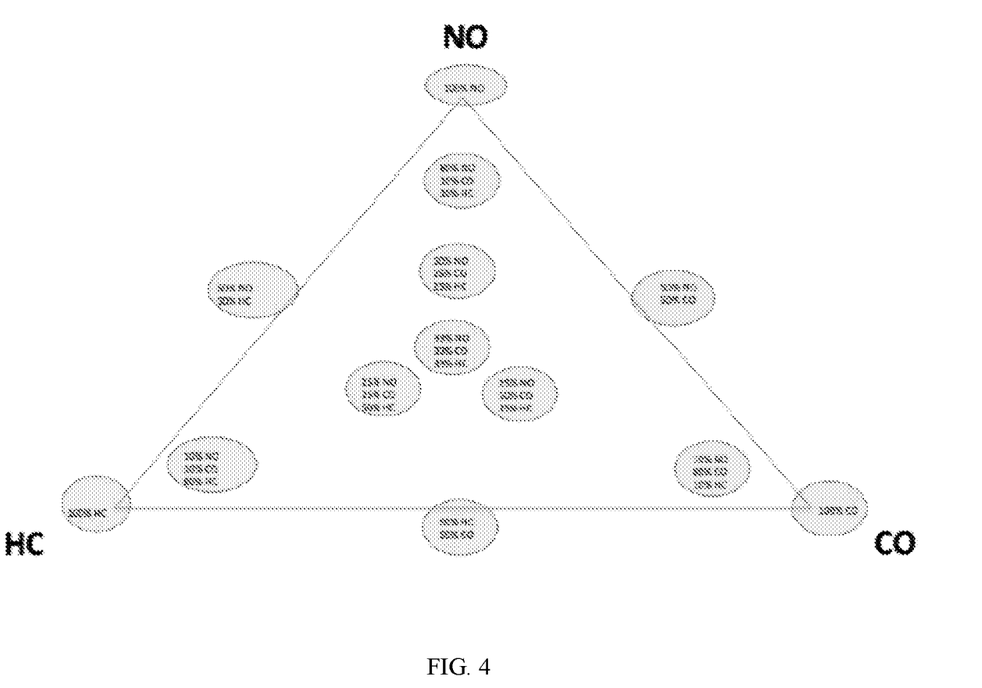
FIG. 4 is a three axis procedural matrix table for a multi-dimensional process, according to an embodiment.

Referring to FIG. 4, in one embodiment, is a three axis procedural matrix table for the multi-dimensional process described herein. FIG. 4 provides one method for putting together a fluid calibration procedure or process. Various combinations of fluidic mixes are introduced and subsequently characterized by their thermal response. The multiple and disparate catalytic surfaces, when measured in iso-fuel, iso-oxygen, and iso-thermal environments, will behave in a repeatable manner to the fluid mixtures so the response surface becomes a lookup table after calibration. This way the fluid concentrations can be deduced by comparing discreet sensing elements response values to the exact same combinations also found in the lookup table, within the measurement error of the embodiment. In this case, a multi-component mixture consisting of 3 active fluids (here, gases) where carbon monoxide (CO), nitric oxides (NOx), and uncombusted hydrocarbons (HC) are shown where the center point is an even mixture (33.3% each), and 100% concentration respectively at each respective vertex of the triangle. This figure illustrates twelve discreet mixtures of the three gases to be flowed past the sensing elements so that a mathematical response surface of reasonable fidelity can be generated (see FIG. 5). Note, even though this is isothermal, iso-oxygen, and iso-flowrate, such parameters and others can be added by creating a more complex procedural table, or multiple similar matrices conducted at varying oxygen, flowrate, or temperature values (as should be appreciated and understood by a person of skill in the art in conjunction with a review of this disclosure).

Figure 5:
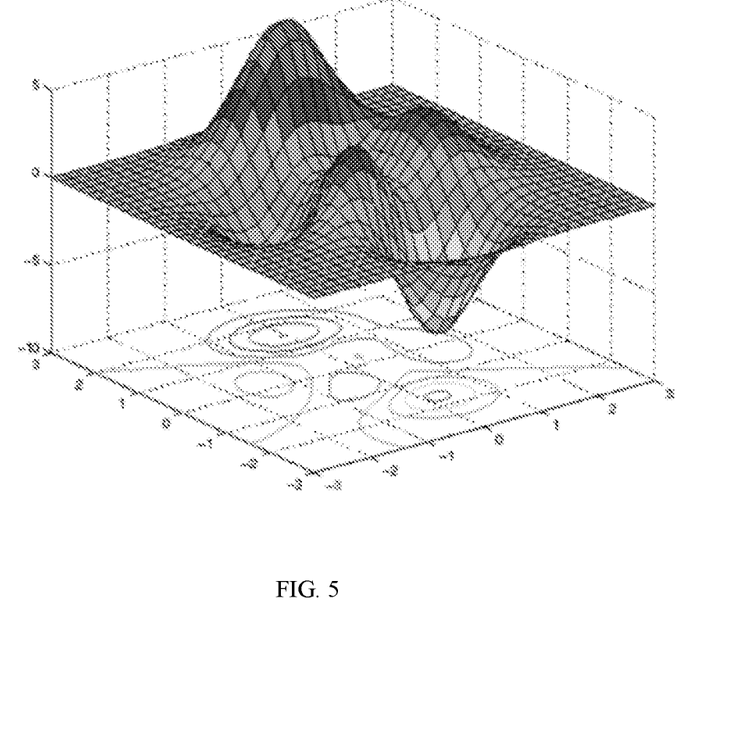
FIG. 5 is a three-dimensional graphical illustration of a notional thermal response surface generated by a notional experimental matrix outlined in FIG. 4, according to an embodiment.

Referring to FIG. 5, in one embodiment, is a three-dimensional graphical illustration of a notional thermal response surface generated by a notional experimental matrix outlined in FIG. 4. In embodiments with surfaces numbering greater than 3 components, this would be a 3D splice taken from a higher order (4D, 5D, or greater) response surface where certain variables are constrained. This notional catalytic response surface illustrates varying exothermic and endothermic responses with the various axes being changes in temperature of the given sensing surfaces in question at the mapped conditions (i.e. varying CO, NOx, HC, etc.) relating to the embodiment in question. This graph shows any deltas as one or more of the measured components are varied, thus forming a poly-dimensional lookup table since each sensing element will have a specific and repeatable response. The number of axes on such a graph is a function of the number of sensing elements plus any external sensors needed to properly account for all variables encountered. Additional dimensions, include but are not limited to, oxygen concentration, fuel consumption, RPM, or post-urea NH3 concentrations. Graphs such as these illustrate the extent and breadth of the software lookup tables/libraries that also constitute embodiments of the present disclosure. It's important to note that FIG. 5 shows only a tiny fraction of the overall response "surface," yet still illustrative of the concepts described herein.

A "module," as may be used herein, can include, among other things, the identification of specific functionality represented by specific computer software code of a software program. A software program may contain code representing one or more modules, and the code representing a particular module can be represented by consecutive or non-consecutive lines of code.

As will be appreciated by one skilled in the art, aspects of the present invention may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowcharts/block diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While several embodiments of the invention have been discussed, it will be appreciated by those skilled in the art that various modifications and variations of the present invention are possible. Such modifications do not depart from the spirit and scope of the present invention.

What is claimed is:

1. A system for determining the concentration of each of an n-number of fluid components in a fluid stream during a first time period, wherein n is an integer equal to 2 or more, the system comprising:
   a housing defining an interior section with a fluid inlet port and a fluid exit port, the housing being configured to accommodate the flow of a fluid stream from the fluid inlet port to the fluid exit port;
   a reference sensor substrate positioned within the housing, connected to a reference sensor and configured to measure a reference temperature value, a reference optical value, or a reference morphological value of the interior of the housing during the first time period;
   an n-number of active sensors, each of which is positioned within the housing and is configured to measure a corresponding deviation of temperature value, optical value or morphological value caused by a presence or an activity of one of the fluid components in the fluid stream within the housing; and
   a processor in communication with each of the n-number of active sensors and configured to determine the concentration of each of the n-number of fluid components in the fluid stream during the first time period by:
      comparing the measured deviation values to combinations of values in a stored library of a plurality of predetermined combinations of deviation values to determine a concentration of each of the n-number of fluid components, each combination of values corresponding to a set of predetermined concentrations of the n-number of fluid components.

2. The system of claim 1, wherein the n-number of active sensors are active catalyst sensors, and the n-number of fluid components are catalyzable fluid components, the system further comprising n-number of temperature sensors, each of which is attached to a respective one of the n-number of different active catalyst sensors, configured to measure the deviation of temperature value at each surface of each of the n-number of different active catalyst sensors.

3. The system of claim 2, wherein at least one of the n-number of different active catalyst sensors comprises a transition metal or transition metal chalcogen.

4. The system of claim 2, wherein at least one of the n-number of different active catalyst sensors comprises a material selected from the group consisting of copper (Cu), platinum (Pt), palladium (Pd), rhodium (Rh), silver (Ag), gold (Au), ruthenium (Ru), iridium (Ir), vanadium oxide ($V_2O_5$), or a mixture of two or more thereof.

5. The system of claim 2, wherein at least one of the n-number of catalyzable fluid components is selected from the group consisting of nitric oxides (NOx), carbon monoxide (CO), uncombusted hydrocarbons (HC) and ammonia ($NH_3$).

6. The system of claim 2, wherein at least one of the n-number of different active catalyst sensors is mounted on an inert substrate.

7. The system of claim 6, wherein the inert substrate is selected from the group consisting of tantalum (Ta) and aluminum nitride (AlN).

8. The system of claim 1, wherein the non-catalytic reference sensor substrate includes a coating selected from the group consisting of tungsten (W).

9. The system of claim 6, wherein the inert substrate is tubular-shaped comprising an outer surface and an inner surface, wherein the at least one of the n-number of different active catalyst sensors is mounted on the outside of the tubular-shaped inert substrate and the respective temperature sensor is mounted to the inner surface of the tubular-shaped inert substrate.

10. The system of claim 2, wherein at least one of the n-number of temperature sensors is selected from the group consisting of a fiber optic temperature sensor, a resistance temperature sensor and a thermocouple.

11. The system of claim 10, wherein the at least one of the n-number of temperature sensors is a fiber optic temperature sensor, wherein the fiber optic temperature sensor is attached to a fiber optic sensor interrogator.

12. A method for determining the concentration of each of an n-number of components in a fluid stream during a first time period, wherein n is an integer equal to 2 or more, the method comprising the steps of:
- providing a system comprising:
    - a housing defining an interior section with a fluid inlet port and a fluid exit port,
    - a non-catalytic reference sensor substrate positioned within the housing and connected to a reference temperature sensor,
    - an n-number of different active catalyst sensors positioned within the housing,
    - an n-number of temperature sensors, each attached to one of the n-number of different active catalyst sensors, and
    - a processor in communication with each of the n-number of temperature sensors;
- providing a fluid stream through the interior section of the housing from the fluid inlet port to the fluid exit port;
- measuring, with the non-catalytic reference sensor substrate, an absolute temperature value of the interior of the housing during the first time period;
- catalyzing the at least one of the n-number of fluid components with a corresponding at least one of the n-number of different active catalyst sensors during the first time period when the fluid stream contacts a surface of each of the n-number of different active catalyst sensors, wherein the catalyst sensors provide deviation of temperature values; and
- determining, using the processor, the concentration of each of the n-number of fluid components in the fluid stream during the first time period by:
    - comparing the measured deviation of temperature values to combinations of values in a stored library of a plurality of predetermined combinations of deviation values to determine a concentration of each of the n-number of fluid components, each combination of values corresponding to a set of predetermined concentrations of the n-number of fluid components.

* * * * *